United States Patent [19]

Wisebaker et al.

[11] 4,382,000
[45] May 3, 1983

[54] CHROMATOGRAPHY DEVICE AND METHOD OF MAKING CHROMATOGRAPHY TEST

[75] Inventors: Sandra M. Wisebaker, Toledo, Ohio; Paul L. White, Ida, Mich.

[73] Assignee: Owens-Illinois, Inc., Toledo, Ohio

[21] Appl. No.: 352,724

[22] Filed: Feb. 26, 1982

[51] Int. Cl.$^3$ ............................................. B01D 15/08
[52] U.S. Cl. .................................. 210/658; 210/198.3; 422/70
[58] Field of Search ................ 210/658, 198.3; 422/70

[56] References Cited

U.S. PATENT DOCUMENTS

| 3,387,710 | 6/1968 | Pogacar | 210/198.3 |
| 3,513,092 | 5/1970 | Matheroe, Jr. | 210/198.3 |
| 3,623,602 | 11/1971 | Valente | 210/198.3 |
| 4,205,058 | 5/1980 | Wagner | 210/658 |
| 4,273,653 | 6/1981 | Ulhlein | 210/658 |

*Primary Examiner*—John Adee

*Attorney, Agent, or Firm*—Richard D. Heberling; Myron E. Click; David H. Wilson

[57] ABSTRACT

There is disclosed a thin layer chromatography device comprising a transparent tube having a first open end adapted for sealing with a stopper, a cylindrical member such as a tube or rod having a diameter smaller than the tube and of a length at least about equal to that of the tube, the member adapted to fit concentrically within the tube, the outside surface of the member being adapted to receive a thin layer of adsorbent before assembly of the member inside the tube, a fitting at the first end of the tube, the fitting having an annular portion defining an opening adapted to receive and hold the member when the tube and member are assembled together to provide a hermetically sealed device before use, at least one sample positioning opening in the tube whereby, upon use of the device, a sample can be positioned on the outer surface of the member and whereby air can enter the interior of the tube.

11 Claims, 5 Drawing Figures

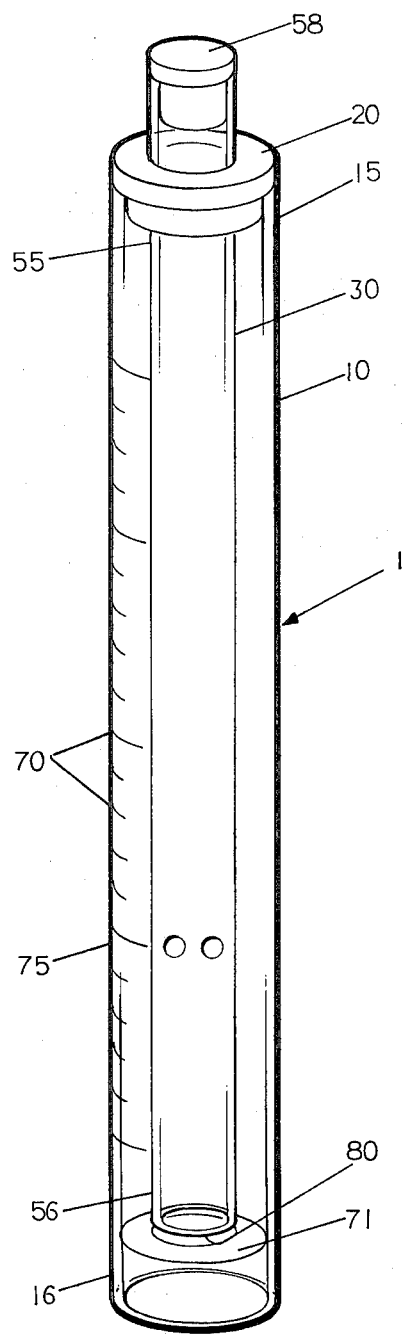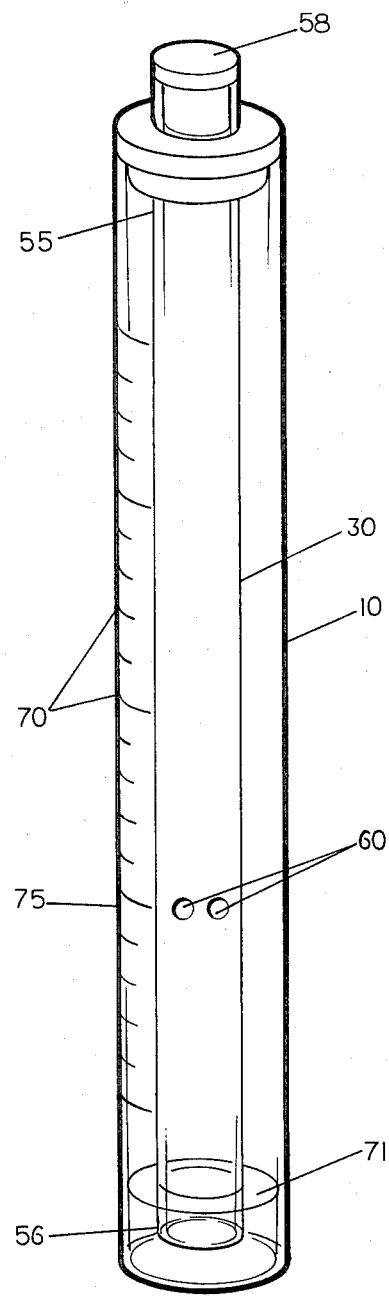
FIG. 1                    FIG. 5

CHROMATOGRAPHY DEVICE AND METHOD OF MAKING CHROMATOGRAPHY TEST

The present invention is directed to a thin layer chromatography device and method of making a chromatography test using the device which is in a transparent tubular form having cylindrical member inside the tube, the member having a thin adsorbent layer on the outside surface.

Thin layer chromatography is a technique for separating chemical compounds by means of a thin layer of adsorbent material. In the past a thin layer of adsorbent material was coated onto a supporting flat plate and the tests conducted thereon. Thin layer chromatography is based on the principles of adsorption, partition, and ion exchange chromatography. A combination of several mechanisms is usually involved, although adsorption is the most common.

When the above described coated plate is immersed in a small quantity of solvent in the bottom of a tank, capillary action causes the solvent to move up the plate through the adsorbent. Continuous competition for active adsorbent sites by the sample and solvent produces fractionization of the sample. Hence components of the sample move different distances along the plate depending upon the affinity for the adsorbent in the solvent. The migration of a component is measured by the $R_f$. It is computed by dividing the distance the component travels by the distance the solvent travels.

U.S. Pat. No. 3,387,710 to Pogacar shows a tube of a transparent material such as glass, the tube having an activated adsorbent coating on its inner surface. The tube has air tight seals at the ends. There are disadvantages and difficulties encountered with the use of such a tubular carrier including the lack of speed, lack of convenience, and inefficiency of chromatography test.

Hence it is desirable to provide a thin layer chromatography device that can serve as an efficient and easily used preliminary screening tool, the screening tool being very useful in the ultimate choice of a more sensitive analytical method.

It is an object of the present invention to provide a thin layer chromatography device comprising a transparent tube having a first open end adapted for sealing with a stopper, a cylindrical member having a diameter smaller than the tube and of a length at least about equal to that of the tube, the member adapted to fit concentrically within the tube, the outside surface of the member being adapted to receive a thin layer of adsorbent before assembly of the member inside the tube, a fitting at the first end of the tube, the fitting having an annular portion defining an opening adapted to receive and hold the member when the tube and member are assembled together, at least one sample positioning opening in the tube whereby a sample can be positioned on the outer surface of the member and whereby air can enter the interior of the tube, and there being a second fitting adapted to fit inside the tube, the second fitting having an annular flange defining an opening adapted to receive and hold an end of the member, the member and second fitting being so constructed and arranged as to provide for sliding movement therebetween.

It is an object of the present invention to provide a thin layer chromatography device comprising a first glass tube having a first open end adapted for sealing with a stopper, a second glass tube of a length at least about equal to that of the first tube, the second tube having a smaller diameter than the diameter of the first tube and adapted to fit concentrically within the first tube, the outside surface of the second tube being adapted to receive a thin layer of adsorbent and binder before assembly of the second tube inside the first tube, a fitting at the first end of the first tube, the fitting having an annular portion defining an opening adapted to receive and hold the second tube when the first and second tubes are assembled together, at least one sample positioning opening in the first tube whereby a sample can be positioned on the outer surface of the second tube and whereby air can enter the interior of the tube, and there being a second fitting adapted to fit inside the first tube, the second fitting having an annular flange defining an opening adapted to receive and hold the second end of the second tube, the second tube and second fitting being so constructed and arranged as to provide for sliding movement therebetween.

It is an object of the present invention to provide a method of making a chromatography test using a thin layer chromatography device, the device comprising a transparent tube having a first open end adapted for sealing with a stopper, a cylindrical member of a length at least about equal to that of the tube, the member having a smaller diameter than the diameter of the tube and adapted to fit concentrically within the tube, the outside surface of the member being adapted to receive a thin layer of adsorbent before assembly of the member inside the tube, a fitting at a first end of the tube, the fitting having an annular portion defining an opening adapted to receive and hold the member when the member and tube are assembled together, at least one sample positioning opening in the tube whereby a sample can be positioned on the outer surface of the second tube and whereby air can enter the interior of the tube, and there being a second fitting adapted to fit inside the tube, the second fitting having an annular flange defining an opening adapted to receive and hold the second end of the member, the member and second fitting being so constructed and arranged as to provide for sliding movement therebetween, the method comprising the steps of:

A. providing a sample on the thin chromatography layer by inserting the sample through the sample positioning opening,
B. placing the bottom of the tube in a solvent,
C. sliding the member into the solvent after the solvent vapor has saturated the interior of the tube, and
D. determining the distances traveled by the solvent and sample in the thin layer.

These and other objects will be apparent from the specification that follows, the appended claims, and the drawings in which:

FIG. 1 is a perspective view of the assembled thin layer chromatography device of the present invention;

FIG. 5 is a perspective view of the assembled device of FIG. 1 with the inside cylindrical member pushed into the down position where the adsorbent coating will contact the solvent.

Figure 2:
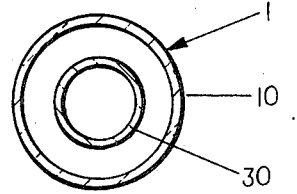
FIG. 2 is a cross-sectional view of the device of FIG. 1.
Figures 3, 4:
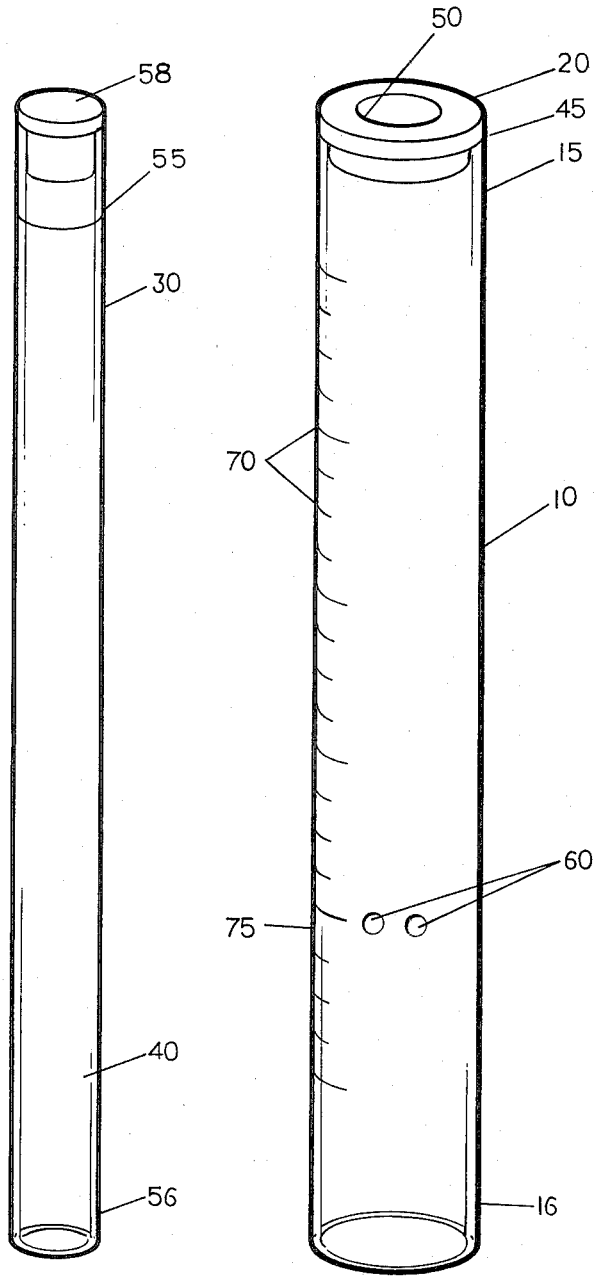
FIG. 3 is a perspective view of the inside cylindrical member before assembly into the device of FIG. 1.
FIG. 4 is a perspective view of the outside transparent tube before assembly into the device of FIG. 1.

As seen in drawings, there is provided an outstanding thin layer chromatography device 1 comprising a first glass tube 10 having a first open end 15 adapted for sealing with a stopper member 20 and a second end 16 adapted for sealing to provide a hermetically sealed tube before use. There is also provided a cylindrical member 30 which is preferably a second glass tube of a length at least about equal to that of the first tube, the second tube having a smaller diameter than the diameter of the first tube and adapted to fit concentrically within the first tube, the outside surface of the second tube being adapted to receive a thin layer of adsorbent 40 before assembly of the second tube inside the first tube. There is provided a fitting portion 45 on the cover 20 at the first end of the first tube, the fitting portion 45 having an annular portion defining an opening 50 adapted to receive and hold the second tube 30 when the first and second tubes are assembled together. As seen in the drawings, the cylindrical member has a first end 55 and a second end 56. The cylindrical member has a suitable sealing member 58 such as a stopper to keep the end clean before use. It is important for efficient use that there be at least one sample positioning opening 60 in the first tube whereby a sample can be positioned on the outer surface of the second tube 30 and whereby air can enter the interior of the first tube 10. There is provided a second fitting 70 adapted to fit inside the first tube, the second fitting having an annular flange defining an opening 80 adapted to receive and hold the second end of the second tube, the second tube and second fitting being so constructed and arranged as to provide for sliding movement therebetween. The tube is hermetically sealed before use (the air vent opening being sealed closed) so that the adsorbent coating can be activated during manufacture and the activation step does not need to be performed again before use.

The thin layer chromatography device is used in the outstanding and efficient method of the present invention of making a chromatography test. The easy to use and straightforward method comprises the steps of:

A. providing a sample on the thin chromatography layer on the cylindrical member through the sample positioning opening in the outer tube, B. placing the bottom 16 of the outer tube in a container of solvent, C. pushing the bottom 56 of the cylindrical member into the solvent as shown in FIG. 5, and D. determining the distances traveled by the solvent and sample in the thin layer.

The method of the present invention includes the step of measuring the distances of the solvent and sample travel on the thin layer, which can be done visually.

The outer transparent tube is made preferably of glass although it can be made of a transparent plastic material such as polymethyl methacrylate, polyester, nylon, polycarbonate, or other clear plastic material. Likewise, the cylindrical member can be made of a clear plastic although glass is preferred.

In accordance with the present invention there is at least one small opening 60 in the outer tube for spotting the sample and getting the sample on to the thin layer coating on the inside of the tube. The opening 60 is important because it provides means to form an air vent on the inside of the tube when the neck end is broken and placed in a solvent to begin the test. The air vent greatly increases the speed of the test.

As seen in the Figures, the present invention provides an adsorbent that is encapsulated preferably in a glass tube with highly advantageous grid markings 70 for easy measurement of the distances that the sample and solvent travel on the adsorbent layer. These distances are easily measured by visual inspection and the sample is easily placed on a zero starting line 75. Hence, the samples are accurately placed inside the tube to provide an easy, convenient and accurate preliminary screening test.

As is well known in the art, suitable adsorbents include silica gel based adsorbents, aluminum oxide, microcrystalline cellulose and silica gel containing phosphor. The adsorbent coating with or without a binder is generally about 0.2 to 0.5 mm in thickness, the preferred thickness being generally about 0.25 to 0.3 mm.

As is known in the art, solvents used in chromatography tests include heptane, cyclohexane, carbon tetrachloride, benzene, chloroform, diethyl ether, ethyl acetate, acetone, methanol and water.

As is known in the art, the adsorbent coating such as one made of silica gel can be activated by heating, say for one hour at 100° C. or more. Thus the tube is dried to activate the adsorbent and the tube can be used without further treatment because it is hermetically sealed.

What is claimed is:

1. A thin layer chromatography device comprising a transparent tube having a first open end adapted for sealing with a stopper, a cylindrical member having a diameter smaller than the tube and of a length at least about equal to that of the tube, the member adapted to fit concentrically within the tube, the outside surface of the member being adapted to receive a thin layer of adsorbent before assembly of the member inside the tube, a fitting at the first end of the tube, the fitting having an annular portion defining an opening adapted to receive and hold the member when the tube and member are assembled together to provide a hermetically sealed device before use, at least one sample positioning opening in the tube whereby, upon use of the device, a sample can be positioned on the outer surface of the member and whereby air can enter the interior of the tube, and there being a second fitting adapted to fit inside the tube, the second fitting having an annular flange defining an opening adapted to receive and hold an end of the member, the member and second fitting being so constructed and arranged as to provide for sliding movement therebetween.

2. A device as defined in claim 1 in which there is indicia on the outside of the tube including grid marks to measure the distance traveled by the solvent and sample in the thin layer.

3. A device as defined in claim 2 in which the indicia includes a zero line for sample spotting and the sample positioning opening located on the zero line.

4. A device as claimed in claim 1 in which the member is a hollow tube.

5. A device as defined in claim 1 in which the member is a solid rod.

6. A thin layer chromatography device comprising a first glass tube having a first open end adapted for sealing with a stopper, a second glass tube of a length at least about equal to that of the first tube, the second tube having a smaller diameter than the diameter of the first tube and adapted to fit concentrically within the first tube, the outside surface of the second tube being adapted to receive a thin layer of adsorbent and binder before assembly of the second tube inside the first tube, a fitting at the first end of the first tube, the fitting having an annular portion defining an opening adapted to receive and hold the second tube when the first and second tubes are assembled together, at least one sample positioning opening in the first tube whereby a sample can be positioned on the outer surface of the second tube and whereby air can enter the interior of the tube, and there being a second fitting adapted to fit inside the first tube, the second fitting having an annular flange defining an opening adapted to receive and hold the second end of the second tube, the second tube and second fitting being so constructed and arranged as to provide for sliding movement therebetween.

7. A method of making a chromatography test using a thin layer chromatography device, the device comprising a first glass tube having a first open end adapted for sealing with a stopper, a second glass tube of a length at least about equal to that of the first tube, the second tube having a smaller diameter than the diameter of the first tube and adapted to fit concentrically within the first tube, the outside surface of the second tube being coated with a thin layer of adsorbent and binder before assembly of the second tube inside the first tube, a fitting at the first end of the first tube, the fitting having an annular portion defining an opening adapted to receive and hold the second tube when the first and second tubes are assembled together, at least one sample positioning opening in the first tube whereby a sample can be positioned on the outer surface of the second tube and whereby air can enter the interior of the tube, and the method comprising the steps of:
  A. providing a sample on the thin chromatography layer on the second tube through the sample positioning opening in the first tube,
  B. placing the bottom of the first tube in a solvent, and
  C. determining the distance traveled by the solvent and sample in the thin layer.

8. A method of making a chromatography test using a thin layer chromatography device, the device comprising a transparent tube having a first open end adapted for sealing with a stopper, a cylindrical member of a length at least about equal to that of the tube, the member having a smaller diameter than the diameter of the tube and adapted to fit concentrically within the tube, the outside surface of the member being adapted to receive a thin layer of adsorbent before assembly of the member inside the tube, a fitting at a first end of the tube, the fitting having an annular portion defining an opening adapted to receive and hold the member when the member and tube are assembled together, at least one sample positioning opening in the tube whereby a sample can be positioned on the outer surface of the second tube and whereby air can enter the interior of the tube, and there being a second fitting adapted to fit inside the tube, the second fitting having an annular flange defining an opening adapted to receive and hold the second end of the member, the member and second fitting being so constructed and arranged as to provide for sliding movement therebetween, the method comprising the steps of:
  A. providing a sample on the thin chromatography layer by inserting the sample through the sample positioning opening,
  B. placing the bottom of the tube in a solvent,
  C. sliding the member into the solvent after the solvent vapor has saturated the interior of the tube, and
  D. determining the distance traveled by the solvent and sample in the thin layer.

9. A method as defined in claim 8 in which there is provided the step of breaking a seal on the sample positioning opening prior to providing a sample on the chromatography layer.

10. A device as claimed in claim 1 in which the sample positioning opening is sealed by an easily breakable glass seal.

11. A device as defined in claim 1 in which the sample positioning opening is sealed by an easily removable plastic cover.

* * * * *